United States Patent
Sicurelli, Jr. et al.

(10) Patent No.: US 6,371,763 B1
(45) Date of Patent: *Apr. 16, 2002

(54) FLEXIBLE POST IN A DENTAL POST AND CORE SYSTEM

(76) Inventors: Robert J. Sicurelli, Jr., 150 Avenue T, Brooklyn, NY (US) 11223; Samuel Masyr, 415 Bay Ridge Pkwy., Brooklyn, NY (US) 11209

( * ) Notice: Subject to any disclaimer, the term of this patent is extended or adjusted under 35 U.S.C. 154(b) by 0 days.

This patent is subject to a terminal disclaimer.

(21) Appl. No.: 09/296,159

(22) Filed: Apr. 21, 1999

Related U.S. Application Data

(63) Continuation of application No. 08/978,867, filed on Nov. 28, 1997, now Pat. No. 5,919,044.

(51) Int. Cl.$^7$ .............................. A61C 5/02; A61C 5/04
(52) U.S. Cl. ..................... 433/220; 433/224; 433/225
(58) Field of Search ................................ 433/220, 224, 433/225

(56) References Cited

U.S. PATENT DOCUMENTS

| | | | | |
|---|---|---|---|---|
| 636,568 A | * | 11/1899 | Seeley | 433/221 |
| 4,894,012 A | * | 1/1990 | Goldberg et al. | 433/215 |
| 5,282,747 A | * | 2/1994 | Nordin | 433/220 |
| 5,326,264 A | * | 7/1994 | Al Kasem | 433/220 |
| 5,328,372 A | * | 7/1994 | Reynaud et al. | 433/220 |
| 5,564,929 A | * | 10/1996 | Alpert | 433/220 |
| 5,890,904 A | * | 4/1999 | Reynaud et al. | 433/220 |

* cited by examiner

*Primary Examiner*—John J. Wilson
(74) *Attorney, Agent, or Firm*—Alfred M. Walker

(57) ABSTRACT

A flexible post for endodontic or reconstructive tooth therapy having a modulus of elasticity which is less than or equal to that of dentin of 18 GPa (giga Pascals). The present invention is preferably made of medical grade optical glass fibers or fiberglass fibers. The micro filaments of the present invention are treated to impart flexibility to each fiber. The fibers are twisted by twisting on other non-axial arrangements of the fibers to impart strength to the unit post. This allows it to function as a permanent post in a tooth. The dental post is flexible and the post conforms to the natural curved contours of a root canal to reduce machining of the tooth and mechanical weakening of the tooth structure.

29 Claims, 6 Drawing Sheets

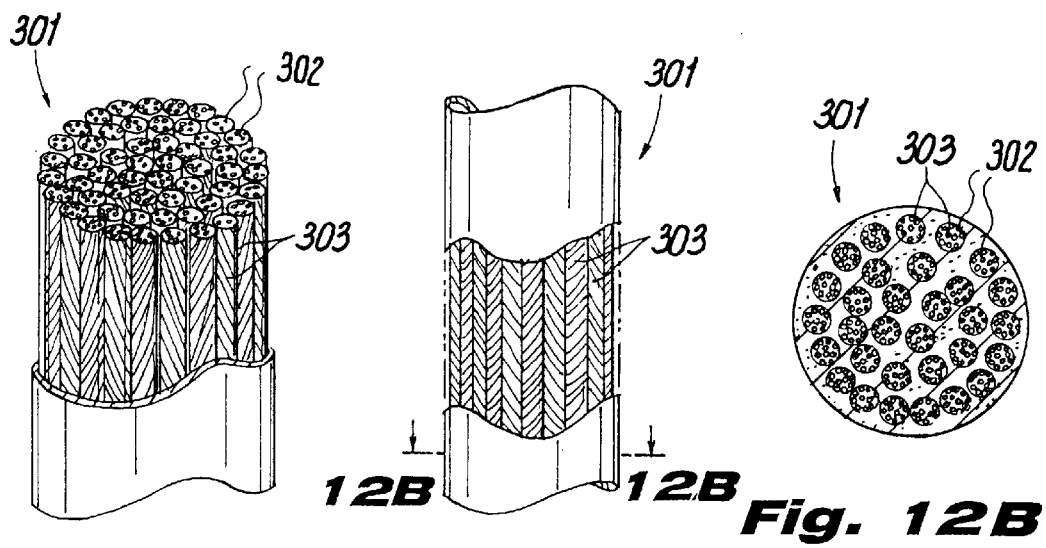
Fig. 12    Fig. 12A    Fig. 12B
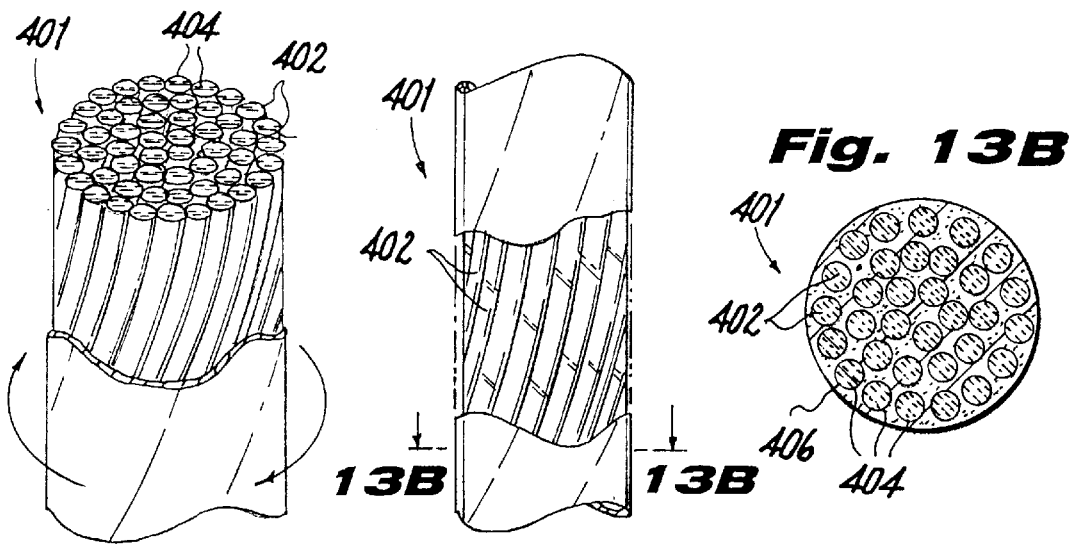
Fig. 13    Fig. 13A    Fig. 13B
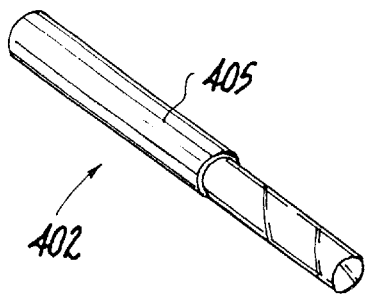
Fig. 13C
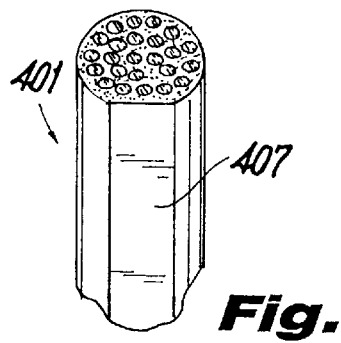
Fig. 13D    Fig. 13E

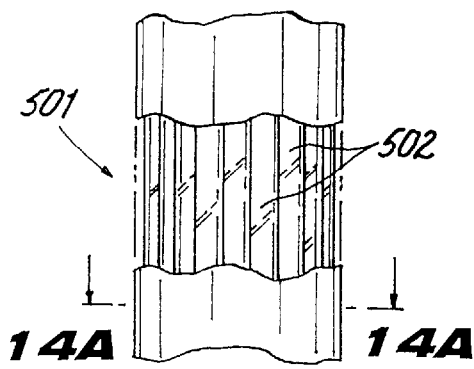
Fig. 14
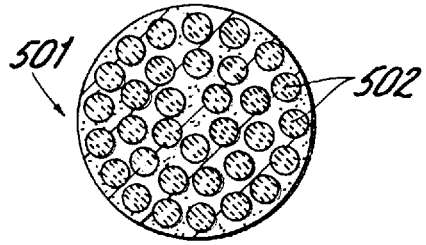
Fig. 14A
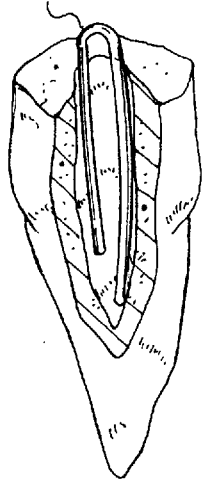
Fig. 15
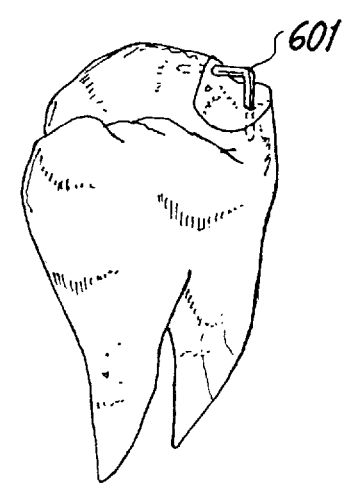
Fig. 15B
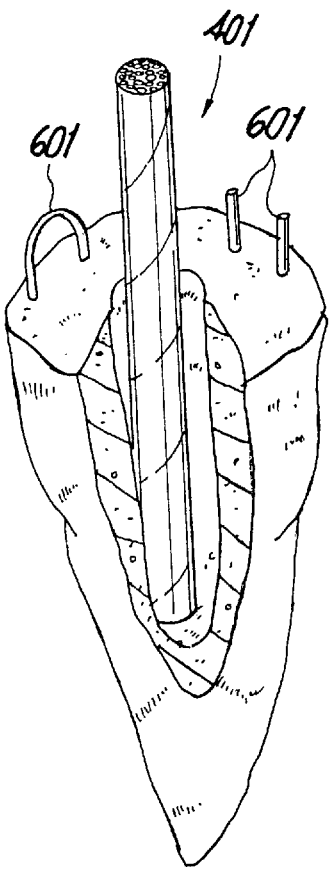
Fig. 15D
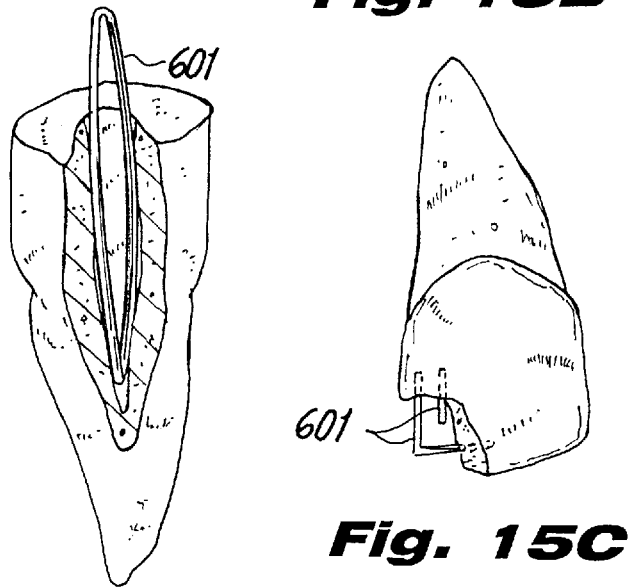
Fig. 15A
Fig. 15C

FLEXIBLE POST IN A DENTAL POST AND CORE SYSTEM

This application is a continuation of Ser. No, 08/978,867 filed Nov. 28, 1997 U.S. Pat. No. 5,919,044.

BACKGROUND OF THE INVENTION

The present invention generally relates to a dental post and core system for endodontically-treated teeth. More specifically, this invention relates to a passive dental post and core system having a flexible inelastic post, wherein the post is made from a material having a plurality of distributed fibers, such as, for example, medical grade optical fibers, other medical grade fibers or other fiberglass materials, which are held together in a matrix in a resin, such as a polyester resin or a vinyl ester resin.

In the preferred embodiment, the flexible post has a modulus of elasticity less than or equal to that of tooth dentin, to prevent widespread damage to a tooth in a traumatic event, when a conventional post would flex less than the tooth dentin, causing tooth fracturing where the flexible dentin violently contacts the inflexible conventional post.

Also in the preferred embodiment, the endodontic post of the present invention is cylindrical, rather than wedge shaped as in many non-metallic posts, because of its less stressful impact and its decreased wedging effect, which can cause immediate and/or residual root fractures.

While the fibers may be axially aligned, preferably at least one of the fibers extends non-axially aligned with respect to a straight axis extending from the apical end to the opposite coronal end of a root of a tooth.

In one embodiment, the present invention includes an endodontic dental reinforcement post for endodontic and reconstructive pin therapy comprising a prefabricated bundle of loosely compacted fibers in a cured resin, with the post extending from an apical end to a coronal end of a tooth canal.

For example, the fibers may be a bundle of fibers, a longitudinally twisted bundle, a twisted braid, a woven lattice, a helically wrapped bundle of fibers, or a composite of randomly dispersed fibers in a binder.

In this preferred embodiment, at least one of the fibers extends non-axially aligned with respect to the straight axis of a root of a tooth.

For example, in a bundle of fibers, while some of the fibers may extend parallel to the straight axis of the root, at least one or more of the fibers extend in an axial direction which is not parallel to the straight axis of a root of a tooth. That is, at least one or more of the fibers extends in a transverse or angled direction away from the straight axis of the root of a tooth.

With respect to a longitudinally twisted bundle, a twisted braid, a helically wrapped bundle of fibers, the twisting or helical wrap of the fibers causes many, but not necessarily all, of the fibers to extend non-axially. Concerning a woven lattice of fibers, while one set of fibers could extend axially parallel to the straight axis of the root, the other intersecting set of fibers extends in a direction which is non-axially aligned with respect to the straight axis of the root. Even if most of the weft of a weave of a plurality of fibers extends parallel to the straight axis of the root, at least one or more fibers constituting the warp of the weave of fibers extends non-axially with respect to the straight axis of the root of the tooth.

Moreover, concerning a composite of randomly dispersed fibers, there is always the possibility of one or more of the fibers being axially aligned to the straight axis of the root of a tooth. However, in order to be randomly dispersed, at least one or more of the fibers extends non-axially with respect to the straight axis of the root of a tooth.

Preferably, the post is radio-opaque and bears a color simulating that of a natural tooth.

Rigid dental post and core systems are widely utilized to restore endodontically-treated teeth. Post and core restorations are routinely used to create an adequate foundation for the final restorative step, which may be a crown, inlay, or a fixed partial denture abutment. Generally, a post is provided for retention and lateral stability of the restoration. The core provides support for the crown. Two general types of post and core systems are known in the art: "active" or screw-in type systems and "passive" type systems. Active post and core systems mechanically engage the walls of the root canal and tooth dentin. Passive post and core systems are bonded in endodontically treated teeth utilizing cements and the like.

Two major problems are encountered when restoring an endodontically-treated tooth. Firstly, the tooth is more susceptible to fracture, and secondly, there is generally less coronal structure with which to work. The greater susceptibility of a tooth to fracture after endodontia may result from the tooth being more brittle. However, studies of the changing mechanical properties of pulpless teeth do not generally support this theory equating dryness with reduced mechanical strength. It appears that the greater susceptibility for fracture in an endodontically-treated tooth results from mechanical weakening of the tooth during root canal therapy and refinement of the root canal. Improvements in restoration techniques that reduce mechanical weakening are therefore desirous.

An endodontically-treated tooth is generally severely compromised either due to trauma or neglect. Thus, traumatic fractures, removal of old restorations and carious tissue, and preparation of root canal access may not leave enough tooth to maintain the "dome effect" of the tooth or to retain a crown.

The stress concentrations in a tooth resulting from the rigid post and core systems of the prior art also play a vital role in tooth fracture. Stress concentrations can be impacted through system design and/or restoration techniques. Various studies and investigations into the susceptibility of endodontically-treated teeth to fracture and the contribution of rigid dental post and core systems to such fracture have been conducted. "A Comparison of Intracanal Stresses in a Post Restored Tooth Utilizing the Finite Element Method", Cailleteau, Johnny G., Rieger, Monty R. and Akin, J. Ed, *Journal of Endodontics*, Vol. 18, No. 11, November 1992, pp. 540–544, reports that placement of a rigid post within a tooth alters the pattern of stress along the root canal as compared with an intact tooth. Instead of strengthening the tooth the post stiffens the coronal posted section and shifts the flexure point apically. The effect of this stiffening causes the non-posted apical portion of the tooth to deform at the post apex, resulting in a stress increase in that portion of the canal wall. Also, the cyclic loading and unloading of an incisor during mastication requires consideration of fatigue failure. Since the maximum bending stresses occur in connection with the apex of the post, any inclusions or defects within the wall of the dentin near the apical end of the post would create stress concentrations that increase the risk of a fatigue crack formation. Defects and microfractures introduced during endodontic treatment and post access preparation could become areas contributing to stress concentrations. Studies have also shown that more intact tooth structure provides better resistance to fracture than a metallic post. There is also evidence that stresses in the tooth tend to increase as the post diameter increases.

A flexible post eliminates these problems and a cylindrical flexible post performs even better. A post and core system utilizing a flexible post shifts the stress concentrations coronally, eliminates the introduction of defects during post access preparation and post placement, and leaves more of the tooth intact.

The main function of a post is to provide retention to the core. Relieved of its expectation to facilitate resistance to tooth fracture, the post can be designed to optimize its retentive properties. Several factors govern the retentiveness of endodontic posts. The shape of the post and its length are among the essential factors.

For example, unlike the preferably flexible cylindrical post of the present invention, tapered dowels have been found to be significantly less retentive than parallel-sided posts. While inflexible metallic posts are generally cylindrical and/or threaded, non-metallic resin-based posts are generally tapered, such as described in French Patent Publication No. 8,515,527 of Barbe et al, published Apr. 10, 1987 or U.S. Pat. No. 5,326,263 of Weissman, where a tapered cylinder is seated within a wide tapered resin base. Such tapering was believed to enhance removal of a first temporary post to be replaced by a permanent post. Weissman '263, also describes a temporary flexible post including a single fiber optic cable rod, which is removed from a reamed, wedged shaped drilled out tooth canal before installation of a permanent, inflexible post. The post of Weissman '263 also has the drawback of being smooth on its surface, to facilitate easy removal of the temporary post.

Weissman '263 also describes a flexible tapered post insertable within a converging, tapered, canal wherein the converging tapered canal is filled with a curable composite. It lacks any texturization of the surface, which helps to maintain a permanent post in position within a tooth canal.

U.S. Pat. No. 5,165,893 of Thompson discloses using a fiber optical plunger applicator to apply a liner adjacent to the inner surfaces of a root canal. It does not describe a permanent post as in the present invention.

A serrated 5.5-mm parallel-sided dowel was found more retentive than an 8-mm tapered post. Tapered posts, such as described in Barbe noted above, provide high shoulder stresses but have an undesirable wedging effect. The wedging effect results in part from the prior art placement of a straight rigid post in a naturally curved and varying diameter root canal.

Furthermore, active threaded posts are very retentive, but may impose too much stress on the tooth, especially compromised teeth.

Thus it appears that a flexible passive, textured, parallel-sided cylindrical post is a preferred structure for dental post and core systems. A flexible, passive, textured parallel-sided cylindrical post provides the previously-mentioned advantages in preventing tooth fracture and additionally permits the post to extend for a greater length into the root canal for improved retention.

In addition to post shape and length, adequate retention is a function of cementing mechanisms. Various cementing medium have been studied. Utilization of low viscosity resin cement in combination with smear layer removal can be considered a universal post cementation technique. In addition to good retention, this cementing technique offers the benefits of a cement with very little resistance to post insertion, thereby minimizing stresses applied to tooth structure during cementation. However, the invention of the present disclosure is not limited by the cementing process used.

Nevertheless, light sensitive cements, such as REVOLUTION®, of E.N.D. Dental Products Company, Somerset, N.J., can only act when used with a translucent substance. Therefore, there is a need for a translucent endodontic post as well.

A major problem of dental posts for endodontic root canal therapy is the inelasticity of posts, even if partially flexible. For example, stainless steel posts have a GPa (giga Pascals) of approximately 190, and titanium posts have a GPa of approximately 100, wherein the higher the GPa number the less elasticity of the post. One attempt to solve this problem is a non-metallic, carbon fiber, unidirectional post known commercially as C-POST® of Bisco Company of Itasca, Ill.

However, its modulus of elasticity is approximately 21, as reported in product literature therefor, whereas natural tooth dentin has a lower modulus of elasticity of 18. Since the modulus of elasticity of the C-POST® exceeds the modulus of elasticity of natural tooth dentin in which the C-POST® is inserted, the C-POST® may cause a tooth to fracture because the C-POST® is less elastic than natural tooth dentin.

Therefore, there is an unsolved need for an endodontic post for root canal therapy wherein the post has a modulus of elasticity less than that of natural tooth dentin. As a result, such a post would have less a likelihood of fracture, and will reduce the need for subsequent re-doing of post and core therapy after a post fractures or extraction of any non-restorable teeth.

Other background art includes an elastic, wire pin having a plurality of flexible, radially extending fins along its length, as is disclosed in German Patent No. DE 3,643,219 to Weisskircher. While providing some advantages over the prior art rigid post, the "high degree of elasticity" of the Weisskircher pin will cause it to try and retain its initial shape in the root canal. During and after placement, flexing of the pin will cause the apical end of the pin to lay against the wall of the root canal. Stress concentrations in the tooth as known for rigid posts will thereby be induced. A pin formed from wire also has low retention characteristics and tends to rotate within the root canal. Radial fins are utilized in the Weisskircher disclosure to resist rotation of the wire pin. However, these radial fins may become further sources of stress concentrations and fatigue failure as the wire pin rotates. No prior art known to the present Applicants discloses or suggests a flexible post in a dental post and core system that is flexible and inelastic, i.e., that conforms to the shape of the root canal to eliminate the stress concentrations that facilitate tooth fracture.

Furthermore, U.S. Pat. No. 4,778,389 to Salvo discloses a dental post construction to eliminate lateral stress in a tooth wherein a rigid, split post is formed by parallel sections joined at a marginal top portion of the post head.

U.S. Pat. No. 5,073,112 to Weil discloses a dental post having an active portion and a passive portion. It also describes a combination sleeve and threaded post, wherein part of the post is threaded, and part is not threaded. A temporary light transmitting rod is inserted to provide light to a light activated composite cement.

U.S. Pat. No. 5,074,792 to Bernadat discloses a passive post and core system comprising a rigid peg disposed in a porous sheath formed of high-strength filaments, wherein the peg has a set of parallel radially extending fins extending from the peg. The filaments in Bernadat are found in the sheath surrounding the peg, not in the peg itself.

U.S. Pat. No. 732,922 of Clark describes a pin for teeth which is flexible, but only by virtue of the fact that the pin includes a base and two tapered pins extending from the base, with a space therebetween, so that the tapered pins can close toward each other within the space.

U.S. Pat. No. 4,952,150 of Schiwiora discloses a tooth root post which includes a tip of solid flexible metal or metal alloys. In contrast to Schiwiora '150, in the present invention, the root post is made of a plurality of metallic or non-metallic fibers, as opposed to a solid piece of metal.

U.S. Pat. No. 4,934,936 of Miller describes a serrated dental post. U.S. Pat. Nos. 622,670 of Dwight and 1,218,289 of Maker both disclose solid threaded posts with a core spacer neck extending therearound.

International Search Publication No. WO 91/07142 (PCT/FR90/00831) to Reynaud et al., which also issued as U.S. Pat. No. 5,328,372, discloses a dental post and core system having a post formed from equally-tensioned fibers of composite material. In Reynaud, the fibers of the composite material are all laid axially within the post and embedded within a resin. Because the fibers are equally tensioned and extend only axially aligned and continuous, any modification of the post in Reynaud may cause a major spreading, continuous, fault line crack in the resin of the post, thus losing integrity of the Reynaud post.

In contrast to Reynaud '372, as noted hereinafter, in the present invention the fibers are loosely compacted and cured in a resin, and not pre-tensioned and stretched under tension by traction, as required in Reynaud et al, as noted in the specification therein.

In further contrast to Reynaud et al, preferably at least one or more of the fibers extends in a direction which is non-axially aligned with respect to the straight axis extending from the apical end to the opposite coronal end of a root of a tooth. Because there is a plurality of directions with respect to the fibers, such as at least one fiber running non-axially, the possibility of a spreading, continuous fault line crack is significantly reduced, thereby achieving unexpected beneficial results not suggested in Reynaud '372. Also, while the Reynaud '372 post can be cut in length, it is contraindicated to shave or adjust the Reynaud '372 post in all directions so that the possibility exists of causing the carbon rods to develop axial fault crack lines.

Other background art includes U.S. Pat. No. 4,936,776 to Kwiatkowski, which discloses a translucent post and core structure to minimize gingival discoloration adjacent a dental restoration, and U.S. Pat. No. 3,949,476 to Kahn discloses a "direct" method of restoring an abraded or broken tooth.

Soviet Union Patent No. SU 1,457,914 of Feb. 15, 1989, to Stomatology Research Institute discloses a method of making a pin stump insert. Moreover, Soviet Union Patent no. SU 1,519,684 of Nov. 7, 1989 describes a threaded grooved tooth implant. Furthermore, Soviet Union Patent no. SU 1,277,950 of Dec. 23, 1986 discloses an electrochemical bonding procedure for coating dental pins.

West German Patent No. 1,541,209 to Kurer discloses the now conventional threaded, screw-in type active post.

U.S. Pat. No. 4,622,012 of Smoler describes a two part dental post system with an outer hollow sleeve post and an inner post insertable within the outer post.

U.S. Pat. No. 4,759,718 of Szeguary describes an active threaded post. U.S. Pat. No. 4,726,770 of Kurer, Swiss Patent No. CH669514 of Polydent, U.S. Pat. No. 4,696,646 of Maitland, and U.S. Pat. No. 4,631,030 of von Weissenfluh, all describe interproximal contact wedge tools for filling cavities in a tooth.

U.S. Pat. No. 5,088,927 of Lee describes a dental plastic member impregnated with metal to enhance x-ray pictures. U.S. Pat. No. 5,030,093 of Mitnick discloses a dental restoration apparatus including a material setting tool which includes an optical probe. U.S. Pat. No. 5,092,773 of Levy describes an apparatus for filling the apex of a root canal with a laser mettable material. U.S. Pat. No. 5,116,227 of Levy describes a laser operable canal forming tool.

French patent application no. FR 2,645,431 of Levy describes a laser tool for cleaning a root canal.

German Patent no. DE 3,411,366 of Neumeyer describes an optical probe for periodental treatment.

U.S. Pat. No. 4,684,555 of Neumeyer describes dental retention pins made of metal, plastic, porcelain or ceramics. However, Neumeyer '555 includes two layers, an inner layer and an outer coating layer. This is in contrast to the present invention, in which there is an even distribution of fibers through the endodontic post. As a result, the post of the present invention requires no outer bond assisting or enhancing layer, as is needed in Neumeyer '555. Furthermore, Neumeyer '555 is not concerned with providing a pin having a modulus of elasticity less than tooth dentin, as is the endodontic post of the present invention.

Other prior art includes U.S. Pat. No. 4,645,457 of Goldman which describes a method of cleaning a root canal prior to installation of a post therein and U.S. Pat. Nos. 4,990,090 and 5,145,373, both of Roane, which describe grooved and/or threaded endodontic posts.

U.S. Pat. No. 5,320,530 of Fong describes an endodontic apparatus for retrofill cavity preparation and U.S. Pat. No. 4,172,867 of Devault describes an index pin and die spacer combination for dental use.

Furthermore, U.S. Pat. No. 5,407,973 of Hasegawa describes a dental cold-polymerizing resin composition and U.S. Pat. No. 5,284,443 of Weil describes a method of inserting a removable light transmitting mandrel point temporarily within a deposit curable composite material, wherein the light transmitting member provides light to cure the material.

In addition, U.S. Pat. No. 5,007,837 of Werly describes a method of filling a cavity and U.S. Pat. No. 822,582 of Carmichael describes an attachment for natural teeth and method of forming the same. U.S. Pat. No. 4,778,388 of Yuda et al describes root canal posts.

European patent application publication no. 0076086 of Carse dated Apr. 6, 1983, describes a threaded dental pin having a threaded pin member and a synthetic resin having a sharing neck 18.

British Patent no. 1,302,022 of Technical Dental Developments dated Jan. 4, 1993 describes an improved dental crown which uses resin with metal particles for casting a crown. It is not for a permanent post.

French Patent publication no. 2,626,167 of Himmel assigned to Compodent Research and Applications Ltd., dated Jul. 28, 1989, also known as British Patent no. GB 2,214,087, describes a dental post pin and a method of making the pin. The dental post pin essentially includes a central filament of yarn which is axially aligned within a sheath of fiber containing resin. Himmel also describes a plastic, ceramic, carbon or glass central wick or filament surrounded by an outer sheath of resin which could have other fibers in it.

In contrast, in the present invention, the fiber bundles preferably are equally dispersed throughout the peg of deposit and are not limited to the central portion. Also, in the present invention, there is no differential of an outer sheath having denser fibers from the loosely packed fibers of the central core.

French Patent publication no. 2,587,197 of Reynaud dated Mar. 30, 1987, and U.S. Pat. No. 4,738,616, also of Reynaud, describe dental posts which are made up of a serial of conical parts that are joined together in a cylindrical conical fashion.

German patent no. DE 3,825,601 of Strobl dated Aug. 9, 1989, describes a dental reconstruction post for endodontics, wherein a fiber reinforced plastic is used. However, there is no mention of the need for imparting flexibility in the post. In Strobl, the fibers are used specifically to strengthen the post and increase rigidity, not to make the post more flexible, as in the post of the present invention.

For example, in paragraph 3 of the section of the patent application of Strobl entitled "State of Technology, with Sources", it is stated that the strength and rigidity of plastics can be increased significantly by incorporating high-strength fibers with a high modulus of elasticity.

In contrast, the endodontic post of the present invention has a low modulus of elasticity, and is thus flexible.

Furthermore, Strobl teaches a wedge shaped post, which increases wedging stress within the tooth. While Strobl discloses rigid, diagonally extending non-axially fibers in the crown stump attached a post, in the post itself the fibers are described as lying in the direction of the root pin, i.e. axially, unlike the preferred embodiment of the present invention.

French Patent publication no. 1,457,914 of Badische dated Dec. 8, 1965, describes a thermal plastic material.

Currently-marketed dental post and core systems such as the FLEXI-POST®; the DENTATUS POST®, the RADIX POST® and the BRASSELEAR® screw posts all advocate screwing threaded rigid posts into straight paths machined into the tooth dentin. These present day posts are also generally formed from rigid metals such as steel, titanium and other alloys which do not flex in the same manner as a natural tooth. As noted before, this differential in flexibility between the natural tooth and the post may cause tooth fracture when the restored tooth is stressed during mastication or from trauma. These cast posts are subject to the same limitations and require an additional laboratory fee and an additional visit to the dentist to complete the procedure.

A means to quickly and easily identify the components of a post and core system is also needed in the prior art. Presently, there is either no color-coding of post and core systems or the color identification consists of an inconspicuous dot of color. Brightly-colored means of identifying post and core systems would significantly advance the art. The lack of a color protocol in the prior art creates confusion, eye strain and a sloppy work environment. The inability to readily identify each post and core by sight creates problems before, during and after the procedure is completed. Firstly, before the procedure is initiated the dentist and staff must select the post and core and isolate it from others that may be very close in size. During the procedure the dentist must carefully avoid confusing the selected post and core. After the procedure the used and unused devices must be readily identified for contamination control. Further, a post and core system installed by one dentist may later require an emergency or other procedure by a different dentist in a completely different part of the world. Color-coded identification would eliminate uncertainty and guesswork.

The post and core system of the present invention overcomes all of these limitations of the prior art.

OBJECTS OF THE INVENTION

A primary object of the present invention is therefore to provide a flexible, inelastic dental endodontic post with a modulus of elasticity less than natural tooth desin.

Another object of this invention is to provide a passive and bondable dental post and core system for endodontically-treated teeth.

Yet, another object of this invention is to provide a dental post and core system that reduces the susceptibility for tooth fracture in endontically-treated teeth.

A further object of this invention is to provide a method for restoring endodontically-treated teeth that reduces the susceptibility for tooth fracture.

Another object of the present invention is to provide a dental post and core system that reduces the mechanical weakening of tooth structure by relieving stress concentrations.

Another object of the present invention is to provide a dental post and core system that reduces the risk of a dentist creating perforations and microfractures during post placement.

It is also an object of the present invention to provide a flexible post in a dental post and core system that automatically adjusts to the contours of a root canal during placement.

Another object of this invention is to provide a post and core system having a flexibility that closely mimics the flexibility of the pulp and dentin tissue of a natural tooth.

Another object of the present invention is to provide a dental post and core system that reduces the amount of time required to restore an endodontically-treated tooth.

It is also an object of this invention to provide a dental post and core system that can be safely and quickly installed by any dentist in a single visit.

Another object of this invention is to provide a dental post and core system formed from material that can be readily shaven to accommodate canal irregularities and in-between root canal sizes without loosing its physical properties.

Another object of this invention is to provide a dental post and core system that is radio-opaque.

Another object of this invention is to provide a method of restoring endodontically-treated teeth that eliminates or nearly eliminates drilling for post placement and that can be installed using inexpensive, readily available endodontic drills.

Another object of this invention is to provide a post in a dental post and core system that fits intimately within a root canal and that accepts standard dental cements.

Another object is to provide a color-coded dental post and core system for identification purposes.

A further object of the present invention is to provide dental post and core system that substantially fits all teeth.

It is another object of the present invention to provide a dental post and core system that can be provided in standardized sizes for mass production efficiencies.

A still further object of this invention is to provide a restoration system of flexible dental pins for teeth previously classified as hopeless and difficult, such as hemisected and dilacereted teeth and other conditions of extreme loss of tooth structure.

These and other objects and advantageous of the improved dental post and core system of the present invention will be apparent to those skilled in the art from the following description of preferred embodiments, claims and appended drawings.

SUMMARY OF THE INVENTION

In keeping with these objects and others which may become apparent, the present invention is a dental post and core system that includes an inelastic flexible post of a bundle of fibers, such as medical grade optical fibers or other fiberglass fibers held together in a resin, such as a polyester resin or a vinyl ester resin.

In contrast to Reynaud '372 in the present invention the fibers are loosely compacted and cured in a resin, and not a pre-tensioned and stretched under tension by traction, as required in Reynaud '372, as noted in the specification therein.

The flexible post conforms to the curvature or path of the root canal during placement and reduces mechanical weakening of an endodontically-treated tooth by eliminating stress concentrations at the apical end of the post, by reducing the size of access preparations and by allowing more intact tooth to be retained.

The present invention also provides a method of restoring an endodontically-treated tooth that reduces the time and equipment needed during a procedure and lessens the chance that a dentist will perforate or fracture the canal wall during placement of a post.

The present invention solves the problems of rigid, inflexible inelastic dental posts for endodontic root canal therapy. For example, stainless steel posts have a GPa of approximately 190 and titanium posts have GPa of approximately of 100 wherein the higher the GPa the less elastic is the post. As noted above, the C-POST® of Bisco Company of Itasca, Ill. is a carbon fiber unidirectional post in an epoxy matrix. However the modulus of elasticity of the C-POST® is approximately 21 whereas the modulus of elasticity of the natural dentin in a tooth is 18. Since the modulus of elasticity of the C-POST® exceeds the dentin it is still subject to fractures because it is less elastic than the natural dentin in the tooth itself.

Therefore while the present invention may closely approximate the modulus of elasticity of tooth dentin, in a preferred embodiment the present invention is directed to an endodontic post for root canal therapy wherein the post has a modulus of elasticity which is less than that of natural tooth dentin. As a result there is a less likelihood of fracture of the post, which avoids a complete extraction of the tooth or need for unnecessary surgery.

One embodiment of the present invention includes using medical grade optical fibers of high optical clarity with high pixel counts of between 50 and a 100 thousand, in a twisted bundle of the linearly extending fibers. Another embodiment uses a twisted bundle of other fiberglass fibers.

The purpose of the slow twist in a bundle of the fibers is as noted in Applicants' prior patent applications, wherein fracture of dental posts can be reduced by removing axial orientation of the fibers in one direction such as in Reynaud or in the C-POST® of Bisco.

The medical grade fiber optic fibers are traditionally used in optical cables which are normally used in the human body for endoscopic visual examination of internal organs through a tube through which the fibers extend.

In this embodiment, the posts of the present invention are made of silica-based fibers, bundled together, having a pure silica core of $SiO_2$. An example of the silica based fibers are medical grade optical fibers from Polymicro Technologies Inc. of Phoenix, Ariz.

The coating of each fiber is a polymer, such as KYNAR® (polyvinylidene fluoride) brand resin, or other resins, such as a polyimide, to impart flexibility to the glass fibers. The coating preferably is chemically or mechanically stripped, so it pulls light out transversally through the stripped apertures along edge of the post. This is beneficial when using a light sensitive adhesive which reacts to light. Typical light activating dental cement in the root, which is adjacent to the posts, include REVOLUTION® bonding light cement of END Dental Products Company of Somerset, N.J. Other non-light activating dental cements include chemical resins, such as SCOTCH BOND® of 3M Corporation of Saint Paul, Minn., or vinyl ester resins.

In the preferable embodiment the silica-based post fibers are coated with PVDF resin which meets USP class VI pharmaceutical standards. Such a resin is known commercially as KYNAR® (polyvinylidene fluoride). KYNAR® (polyvinylidene fluoride) fluoro-polymers are strong, as reflected by their tensile properties and impact strength. They have an excellent resistance to fatigue. However, they are useful in endodontic posts since they are flexible and light transmitting, and they are resistant to mechanical stresses. According to ASTM test D638 they have tensile strength of 5,000 to 6,500 psi yield. They have a tensile modulus according to ASTM test D882 of 150 to 200×103 psi.

Moreover, the crystalline state of the KYNAR® (polyvinylidene fluoride) brand resins can be modified in rapid cooling to promote smaller crystalline size with increased crystallinity of their higher values for yield strengths. The KYNAR® (polyvinylidene fluoride) polymer and KYNAR® (polyvinylidene fluoride) flex co-polymer grades are in compliance with U.S. Pharmacopia (USP) classification VI.

In an alternate embodiment, E-glass fiberglass fibers are used as a substitute for the silica optical fibers. E-glass is commonly used in the electronics industry; a typical composition is 55% SiO2, 16% CaO, 15% Al2O3, 10% B2O3 and 4% MgO. This composition can be altered to achieve preferred properties for this application as described above.

While other size fibers may be used, a typical fiber of the group making up the bundle of fibers, is one thousandth of an inch in diameter. Therefore, a bundle of two hundred fibers has a diameter of approximately 0.05 inch. The final post peg may therefore be also 0.05 inch in diameter, including approximately 200 fibers plus the saturation of the epoxy binder with an optional colorant/opaquer mixed into the epoxy resin to modify and change these properties.

As an alternative to adding an opaquer mix into the epoxy resin, one or more metal fibers or wires at or near the center of the fiber bundle can be used. This would have the added advantage of providing a ready means to remove the post (if this were necessary) by the following method. The single centrally located wire or fiber can be pulled out leaving a pilot hole for guidance of a reamer to facilitate removal.

A preferred embodiment for an epoxy resin in MASTER BOND® Polymer System EP21LV of Master Bond, Inc. of Hackensack, N.J. MASTER BOND® is a two component, low viscosity epoxy resin in which the fibers are cast. The rigidity of MASTER BOND® can be adjusted by adjusting the mix ratio of the two components. Other useful resins include polyester resins or vinyl ester resins. Depending upon the adjustment of the epoxy resin, the number of fibers can vary.

Preferably the bundle of fibers have a rounded end and may also have a tapered end with an optional continuous groove or facet of 50 to 100 micron depths to increase [su]rface texturing. The standard length of the post is about ⅝ inch and the standard diameter is about 0.04 inch to 0.05 inch, with an optional taper at the top with ⅛ inch linearly. The texturing may be by a die drawn across linearly or axially of 50 to 100 micron depth or it may be etched with acid or laser lights such as carbon dioxide laser or Yag laser or there may be an outer skin sheath added which is texturized. The individual fibers in one post in bundles are optionally twisted or gathered as they come off a spool.

Optionally the post may be tooth colored by adding barium sulfate to the epoxy resin that holds the bundle of fibers together such as in a medical grade epoxy such as bisGMA.

Among other uses for which the fiber based posts may be used is as a dental cavity reconstructive pin to replace titanium, steel, or gold pins which tend to corrode and which do not have a good modulus of elasticity.

This optional use for the fiber based post is as a reconstructive pin for a tooth with large areas of decay or traumatic damage. Such a tooth may be reconstructed using pins as a lattice scaffolding to stabilize the filling. Most prior art pins are metallic which has colorization problems. Furthermore, the flexible pin of the present invention can be looped around and closed into the tooth wherein the canal is back filled with composite material. The looping helps with retention by exerting a lateral force against the inside of the canal to provide an anti-rotational feature for both the post and the pin, wherein the axially extending surface facet is cut.

Other possible uses of the present invention are for hip prosthesis, finger joint restoration or other types of bone implants, to reduce resorption bone dissolution due to stress or infections.

In summary, while in some embodiments, the modulus of elasticity of each post is above, but close to, that of tooth dentin, the preferred embodiment has a modulus of elasticity which is less than that of the tooth dentin, which is about 18 GPa (giga Pascals).

In contrast to this embodiment of the present invention, in the Weissman '263 post, the reamer does not require any specialized shape at its end as long as its diameter is essentially the same as the diameter of the posts. The Weissman '263 posts are easily deformable. Also Weissman '263 describes a temporary fiber optic rod which is removable from a central channel.

In contrast, the present invention is a permanent, flexible post which has fiberglass fibers, or medical grade optical glass fibers, making it an integrally strong post. The micro filaments of the present invention may be treated by coating to impart flexibility and strength to each fiber. This is not done to add flexibility to the unit post but is done to effect the twisting or other non axial arrangements of the fibers to impart strength to the unit post. This allows it to function as a permanent post in all teeth, not only as a temporary post as in Weissman '263. Furthermore, the Weissman '263 post requires a composite cement or encasement, which is polymerized by using a bonding light, whereas the present invention can use either a light activated cement or a chemically cured cement, such as a glass ionomer which requires no photo activation.

Moreover, in the preferred embodiment of the present invention, the post is textured to keep it bonded in the canal, whereas the Weissman '263 post has a smooth surface to intentionally allow it to be removed because it is a temporary post. It has only been suggested to use the Weissman '263 post as a permanent post in compromised teeth, because the Weissman '263 post may lack mechanical properties such as tensile shear and compressive strengths.

In another embodiment of the dental post and core system of the present invention, the post includes a core spacer and a flexible, post reinforcing rod extending apically from the core spacer. The core spacer may be flexible, resilient or otherwise deformable and may be selectively attachable or integrally formed with post reinforcing rod. A core may be selectively attached to the upper portion of the core spacer, integrally formed with the core spacer or built-up to custom specifications.

A further embodiment of the present invention is a mutable flexible post. The mutable post of the present invention comprises a bundle of fibers that may be selectively flared at the coronal aspect to provide a core seat or to provide extra surface area to scaffold a core.

BRIEF DESCRIPTION OF THE DRAWINGS

The present invention can best be understood in conjunction with the following drawings, in which:

FIG. 12 is a perspective view of a portion of the flexible post of another embodiment for the present invention;

FIG. 12A is a side elevational view of a portion of the post as in FIG. 12;

FIG. 12B is a top plan view in cross section of the post as in FIG. 12, taken along line 12B—12B of FIG. 12A;

FIG. 13 is a perspective view of another embodiment including a group of fibers therein, for use in making a flexible post;

FIG. 13A is a side elevational view of the portion of the fiber as in FIG. 13;

FIG. 13B is a top plan view in cross section of the post as in FIG. 13, taken along line 13B—13B of FIG. 13A;

FIG. 13C is a close up perspective view of one fiber used in the embodiment shown in FIG. 13;

FIG. 13D is a close-up perspective view of the embodiment shown in FIG. 13, shown with an optional axially extending facet.

FIG. 13E is a cross sectional plan view of the embodiment shown in FIG. 13D.

FIG. 14 is yet another embodiment for a flexible post;

FIG. 14A is a top plan view of the post in FIG. 14, taken along line 14A—14A of FIG. 14;

FIGS. 15–15D show an alternate embodiment for a dental reconstructive pin;

DESCRIPTION OF THE PREFERRED EMBODIMENTS

Figure 1:
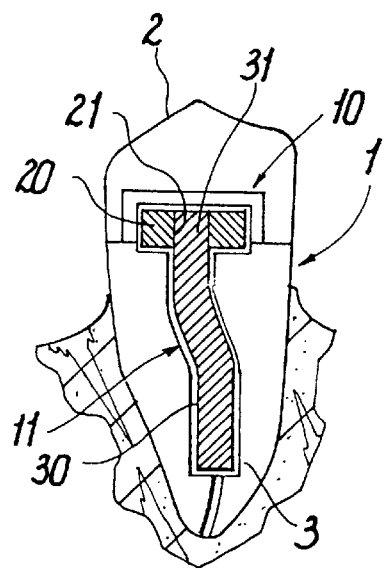
FIG. 1 is a lateral cross-sectional view of the first preferred embodiment of the dental post and core system of the present invention.

FIG. 1 illustrates a lateral cross-sectional view a first preferred embodiment of the dental post and core system 1 of the present invention. First system 1 generally comprises a core 10 and flexible post 11. Post 11 includes a core spacer 20 and a flexible inelastic post reinforcing rod 30 extending apically from the core spacer 20. The post reinforcing rod 30 may be cylindrical or tapered. Further, core spacer 20 may be flexible and/or resilient. In the first dental post and core system 1, core spacer 20 and reinforcing rod 30 are shown to be separately constructed. A bore 21 in core spacer 20 selectively engages an upper portion 31 of post reinforcing rod 30. However, core spacer 20 and reinforcing rod 30 may be integrally formed without departing from the spirit and scope of the present invention. The separable construction of core spacer 20 and the reinforcing rod 30 permits fabrication of built-up post and core systems 1 in a variety of configurations from readily identifiable components.

Core 10 is seated on the core spacer 20 and a crown 2, for example, is placed over the core 10 as known in the art.

The teachings of the present invention may be utilized for restoration of multi-rooted teeth having two, three or four diverging canals. In the second dental post and core system 1' for a double-rooted tooth illustrated in FIG. 2 it can be seen that said second system 1' includes a second core spacer 20' having two bores 21a, 21b which engage respective flexible post reinforcing rods 30.

The advantages of a flexible post 11 in a dental post and core system are numerous. Firstly, a flexible post 11 can follow the contours of the root canal 3. This method of placement eliminates or reduces the amount of drilling required for root canal therapy and for preparation of the canal access. The reinforcing rods 30 can be appropriately sized to permit use of commonly-used dental drills. More intact tooth is left in place which has been shown to provide the best resistance to tooth fracture. The flexible post reinforcing rod 30 of the present invention also eliminates stress concentrations in the canal wall and dentin due to the apical lateral movement of rigid posts. Utilizing a flexible post 11 the intracanal stress at the apical level is shifted coronally to the area of maximum stress. The core spacer 20 absorbs the intracanal stresses by deformation of the body of the core spacer 20. Core spacer 20 therefore can be seen to serve as both a seat for the core 10 and as a stress absorber. A flexible post 11 also reaches further apically which provides greater retention. This is specifically applicable to the restoration of teeth that have suffered extreme loss of tooth structure where to gain adequate retention the length of the post must enter the curved portion of the root canal 3.

Figure 3:
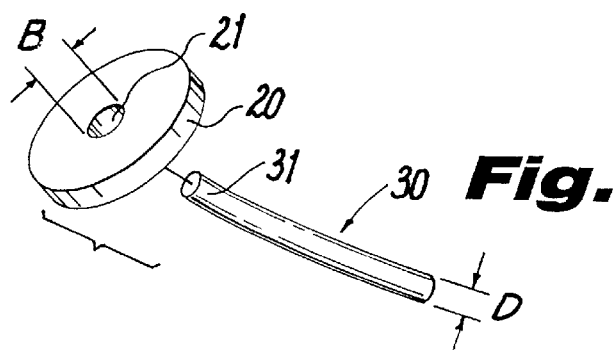
FIG. 3 is a perspective, exploded view of a first core spacer and a first post reinforcing rod of the present invention.

In the first preferred embodiment of the flexible post 11 in the first dental post and core system 1 of the present invention, illustrated in an exploded, perspective view in FIG. 3, the core spacer 20 and the flexible post reinforcing rod 30 are formed from identical material. This, however, should not be understood to be a limitation of the present invention. The core spacer 20 may be formed of a first material to optimize its stress resistance characteristics, reinforcing rod 30 may be formed of a second material to optimize its retention characteristics.

Core spacer 20 and post reinforcing rod 30 are preferably formed from reinforced plastics such as medical grade optical fibers, or fiberglass polyester composites similar to those used in the construction of fishing poles, flexible ceramic resin composites, graphites, teflons, polycarbonates and the like. Metals, such as pure or alloyed titanium, steel, platinum, palladium and the like, can be processed into fibers and bound in a matrix of resin or other binders for fabrication of the core spacer 20 and post reinforcing rod 30. The flexibility of these materials is close to the flexibility of the natural tooth and therefore will reduce the flexibility differential of the intact tooth and the inserted post 11. Fiberglass polyester composites and the like are also well suited for in-office etching of the surfaces of the core spacer 20 and reinforcing rod 30 for better and stronger cementation. Reinforcing rod 30 may also be treated with dental adhesives and bonding agents such as silane urethane, bisGma and acrylic resins to increase retention. Core spacer 20 and post reinforcing rod 30 also preferably include an appropriate amount of radio-opaque material such as titanium oxide, barium sulfate and other materials known in the dental industry to insure X-ray documentation.

The first preferred embodiment of the flexible post 11 is preferably color coded for identification purposes. In the first preferred flexible post 11, the core spacer 20 and reinforcing rod 30 are color identified according to the inside diameter of the bore 21 in core spacer 20, identified in FIG. 3 by the letter "B", and the outside diameter of the reinforcing rod 30, identified in FIG. 3 by the letter "D". In the preferred embodiment the reinforcing rods 30 are formed having the following diameters "D": 0.036 inch, 0.040 inch, 0.050 inch, 0.060 inch, and 0.070 inch. The bores 21 of the respective core spacers 20 have a corresponding bore diameter "B" (marginally larger than rod diameter "D") for snug engagement of the spacer 20 to an upper portion 31 of the post reinforcing rod 30. Bright colors are preferably used. The following color protocol is preferred:

| "B", "D" | Color |
|---|---|
| .036 inch | White |
| .040 inch | Yellow |
| .050 inch | Red |
| .060 inch | Blue |
| .070 inch | Green |

Figure 2:
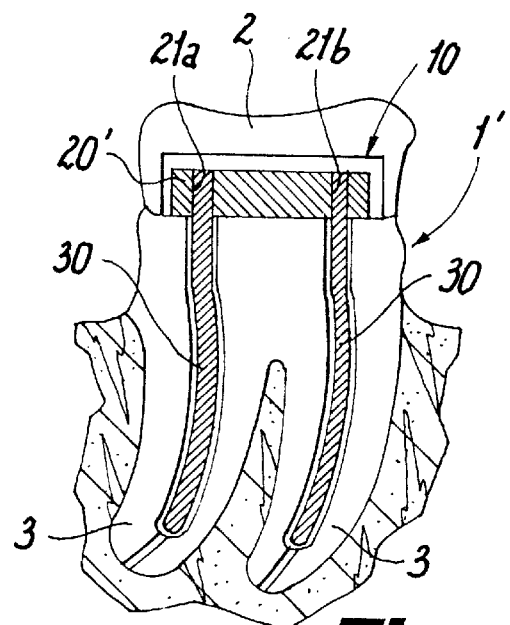
FIG. 2 is a lateral cross-sectional view of a first preferred embodiment of the present invention in a double-canal tooth.

A second dental post and core system 2 for multi-rooted teeth, as illustrated in FIG. 2, may have a second core spacer 20' wherein the respective first and second bores 21a, 21b are sized differently for placement of reinforcing rods 30 of different size. Prefabricated multiple root dental post and core systems 2 having differently sized reinforcing rods 30 will be multicolored in accordance with the above protocol. For example, a second core spacer 20' may have a yellow ring around first bore 21a and a white ring around second bore 21b to indicate that this core spacer 20' is to be utilized with a 0.040 inch reinforcing rod 30 in first bore 21a and a 0.036 inch reinforcing rod 30 in second bore 21b.

Figure 4:
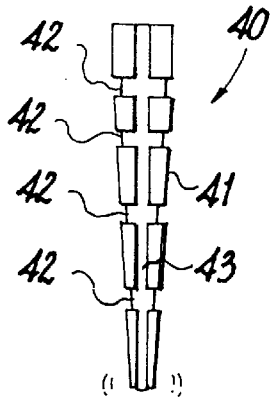
FIG. 4 is a lateral cross-sectional view of a second post reinforcing rod constructed in accordance with the teachings of the present invention.

FIG. 4 illustrates in a front plan view a second preferred embodiment of a reinforcing rod 40 constructed in accordance with the teachings of the present invention. Second reinforcing rod 40 is a tapered, having flexible elongated member 41. The outer wall of the elongated member 41 includes a plurality of displaced circumferential serrations 42 and a channel 43 extending longitudinally between the respective serrations 42. The combination of flexibility in the second reinforcing rod 40 and the displacement of the respective serrations 42 is believed to reduce the wedging effect of rigid posts as known in the art.

Figure 5:
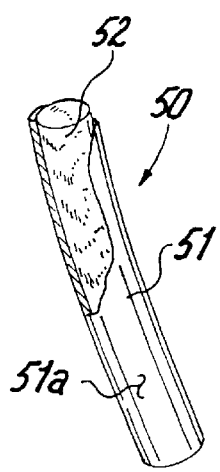
FIG. 5 is a partially cross-sectioned perspective view of a third post reinforcing rod constructed in accordance with the teachings of the present invention.

A third preferred embodiment of a reinforcing rod 50 is illustrated in FIG. 5. Third reinforcing rod 50 comprises a closed flexible sheath 51 having a compressible gel 52 disposed within the interior of the sheath 51. During placement of the third reinforcing rod 50 the wall 51a of the sheath 51 deforms to the varying diameter and curvature of the root canal.

From the foregoing, it should be readily understood that the respective first, second and third reinforcing rods 30, 40 and 50 may be utilized in conjunction with a core spacer 20 or a prefabricated or built-up core 10 may be attached directly to the coronal end of the reinforcing rod 30, 40, 50. A prefabricated core 10 for attachment directly to a reinforcing rod 20, 40, 50 may include a bore 21 extending therethrough as illustrated for the core spacer 20 of the present invention. Reinforcing rods 30, 40 find 50 may be pre-cut or formed in an extended length to provide a margin of safety for mistakes in measuring.

Figure 6:
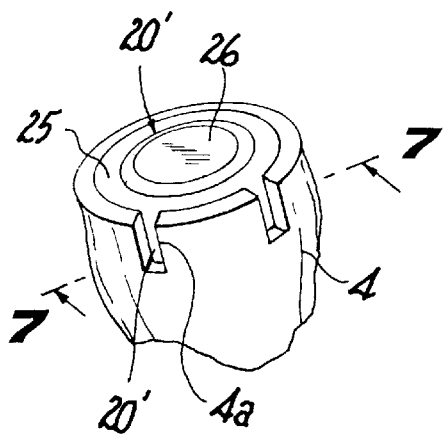
FIG. 6 is a top perspective view of a second built-up core spacer in accordance with the teachings of the present invention.
Figure 7:
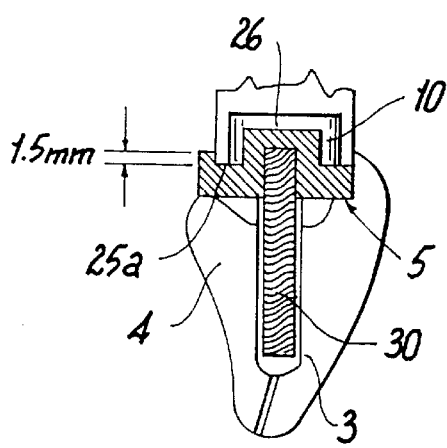
FIG. 7 is a lateral cross-sectional view taken along line 7—7 of FIG. 6.

The core spacer 20 of the present invention may be prefabricated in standard sizes or built-up in the dentist's office. The external shape of core spacer 20 generally corresponds to the concavity of the chamber termed in root canal therapy. In teeth with a shallow concavity, standard dental drills may be used to machine a countersunk region 5 in the tooth (FIG. 7) for receipt of core spacer 20 or a built-up core spacer 20'. FIGS. 6 and 7 illustrate a preferred embodiment of a built-up core spacer 20' constructed in accordance with the teachings of the present invention. The flexible reinforcing rod 30 is placed into the root canal 3 (FIG. 7). Built-up core spacer 20' is then formed about the coronal end of first reinforcing rod 30 by injection of any of the suitable fast-setting liquids or pastes known in the art. Built-up core spacer 20' initially extends to the top of the tooth dentin 4 and into any fractures 4a or the like in the tooth. A recessed ring 25 is then countersunk into the top of the built-up core spacer 20' along the inside edge of the tooth to form a central, raised portion 26 of the built-up core spacer 20'. It is preferred that the floor 25a of the recessed ring 25 is approximately 1.5 mm below the top of the tooth dentin 4. As can be seen in the cross-sectional view of the built-up core spacer 20' illustrated in FIG. 8, a core 10 is seated onto the top of the central, raised portion 26 and the floor 25a of the recessed ring 25. Preferably, sufficient lateral space is left so that the crown 2 may be fitted over the core 10 to likewise rest on the floor 25a of the recessed ring 25 approximately 1.5 mm below the top of the tooth.

Figure 8:
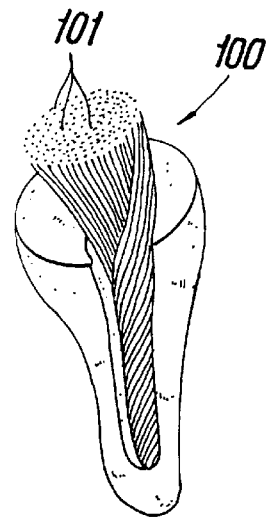
FIG. 8 is a perspective view of a second preferred embodiment of the dental post and core system of the present invention.
Figure 9:
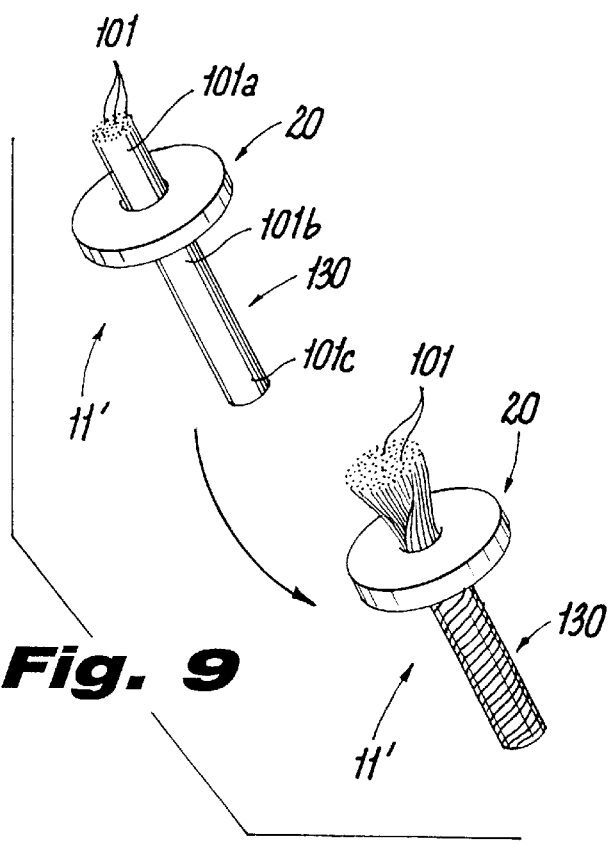
FIG. 9 is a perspective view of a third preferred embodiment of the dental post and core system of the present invention.

A mutable flexible post 100 is illustrated in FIG. 8 and a mutable post reinforcing rod 130 is illustrated in FIG. 9. Mutable post 100 and mutable post reinforcing rod 130 are preferably formed from a bundle of reinforced plastic or other fibers 101 cemented together at the central portion 101b and the lower portion 101c of the fibers 101. The upper portion 101a of the fibers 101 is loosely compacted so that the upper portion 101a may be selectively flared to provide additional surface area to scaffold a built-up core. Flaring of the upper portion 111a of the fibers 101 may be performed at the factory or in the dentist's office using standard crimping pliers. A prefabricated core (not shown) may be attached to the coronal aspect of the mutable post 100 when it is disposed in its unflared position.

As shown in FIG. 9 the mutable reinforcing rod 130 constructed in accordance with the teachings of the present invention may likewise be utilized in a flared or unflared position. A first core spacer 20 is attached to the coronal end of the mutable reinforcing rod 130. The mutable post 11' comprising a first core spacer 20 and a mutable reinforcing rod 130 may be used to support a prefabricated core, or the coronal end of the mutable post 11' may be flared to form a scaffold for a built-up core. An advantage of this preferred embodiment of the present invention is that a single construction can be used for either a prefabricated dental post and core system or a mutable post reinforcing rod 130 to support a built-up core.

Post 11 may be made without core spacer 20. Moreover, post 11 may be made from a material having a plurality of distributed fibers, such as medical grade optical fibers, wherein at least one of the fibers extends non-axially aligned with respect to a straight axis extending from the apical end to the opposite coronal end of a root of a tooth.

For example, the fibers of post 11 may be a bundle of fibers, a longitudinally twisted bundle, a twisted braid, a woven lattice, a helically wrapped bundle of fibers, or a composite of randomly dispersed fibers in a binder.

In the preferred embodiment, at least one of the fibers of post 11 extends non-axially aligned with respect to the straight axis of a root of a tooth.

Figure 10A:
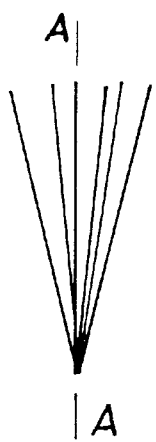
FIGS. 10A–10I show various embodiments for a dental post and core system wherein at least one or more of the fibers constituting the post are non-axially aligned with respect to axis A—A extending from the coronal end to the apical end of a root of a tooth.

For example, in a bundle of fibers, such as the conical bundle of fibers shown in FIG. 10A, while some of the fibers may extend parallel to the straight axis A—A of the root, at least one or more of the fibers extend in a non-axial direction which is not parallel to straight axis A—A of a root of a tooth. That is, at least one or more of the fibers extends in a transverse or angled direction away from the straight axis A—A of the root of a tooth.

Figure 10B:
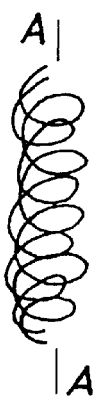
Figure 10C:
Figure 10D:
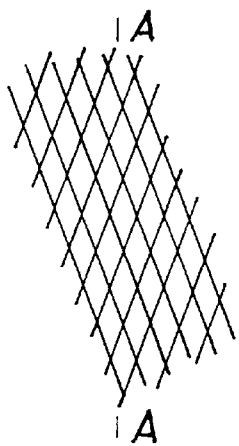
Figure 10E:
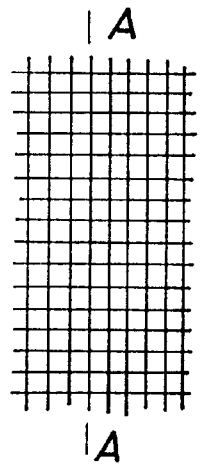
Figure 10F:
Figure 10I:
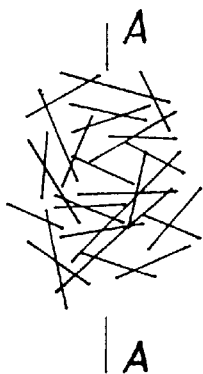
Figure 10H:
Figure 10G:

With respect to a longitudinally twisted bundle, such as shown in FIG. 10H, a twisted braid, such as shown in FIG. 10C, a helically wrapped bundle of fibers, such as shown in FIG. 10B, the twisting or helical wrap of the fibers causes many, but not necessarily all, of the fibers to extend non-axially. Concerning a woven lattice of fibers, such as shown in FIGS. 10D or 10E, while one set of fibers could extend axially parallel to the straight axis A—A of the root, the other intersecting set of fibers extends in a direction which is non-axially aligned with respect to the straight axis A—A of the root. Moreover, as shown in FIG. 10G, even if most of the weft of a weave of a plurality of fibers extends parallel to the straight axis A—A of the root, at least one or more fibers constituting the warp of the weave of fibers extends non-axially with respect to the straight axis of the root of the tooth. Furthermore, as shown in FIG. 10F, instead of a true weave, a bundle of axially aligned fibers may have at least one or more non-axially aligned fibers constituting a strap collar containing the remaining fibers (whether axially aligned or not) therein.

While the bundles of fibers shown in FIGS. 10A–10I are shown without core spacers, such as core spacer 20 in FIG. 1, similar core spacers may alternately be provided, or the ends of the bundles of fibers may be flared, such as shown in the conical bundle in FIG. 10A or the twisted bundle shown in FIG. 10H.

As shown in FIG. 10I, concerning a composite of randomly dispersed fibers, there is always the possibility of one or more of the fibers being axially aligned to the straight axis A—A of the root of a tooth. However, in order to be randomly dispersed, at least one or more of the fibers extends non-axially with respect to the straight axis A—A of the root of a tooth.

The fibers in FIGS. 10A–10I may be formed from metal or non-metallic fibers in a composite, such as within a plastic material. Alternately, the coronal end may be flared by loose compacting of the coronal end, or by mechanical undercutting of the coronal end.

In addition, the post is both flexible and inelastic, so that the post can bend but generally maintain its original length. For example, in flexing, one side is extended, and the other side is compressing about an axis.

Figure 11:
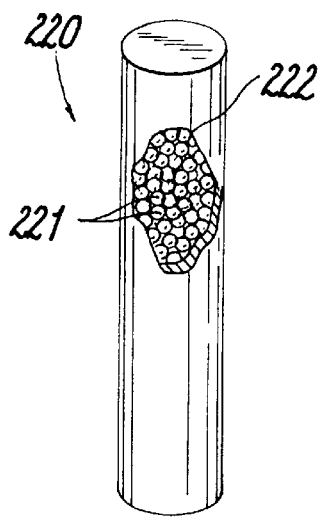
FIG. 11 is a perspective view in partial section of an alternate embodiment for a flexible inelastic post with a plurality of randomly dispersed particles within a binder.

FIG. 11 is a perspective view in partial section of a further alternate embodiment for a flexible inelastic post 220 with a plurality of randomly dispersed particles 221, such as beads or other shaped particles, within a binder 222.

As shown in FIGS. 12–14, an endodontic post 301 for root canal therapy has a modulus of elasticity which is less than or equal to that of tooth dentin, thus reducing the risk of fracture of the post. In the embodiment shown in FIGS. 12, 12A and 12B, post 301 preferably includes optical fiber filaments 302 making up fiber bundles 303, in a twisted bundle of the linearly extending fiber bundles 303.

Optionally, fibers 302 may be other fiberglass fibers.

The purpose of the slow twist or other geometric arrangement in the bundle of the fibers 303, is to reduce fracture lines in the dental posts that could develop from shaving or adjusting the post size by removing axial orientation of the fibers 303 in one direction, such as in the aforementioned C-POST® of Bisco.

Filaments 302 of fibers 303 may be fiber optic fibers in cables which are normally used in the human body for endoscopic visual examination of internal organs through a tube through which the fibers extend.

In another embodiment shown in FIGS. 13, 13A, 13B and 13C, instead of a group of filaments 302 forming a fiber 303, in this preferred embodiment, post 401 is made of a generally cylindrical bundle of optical fibers 402 which are twisted when bundled together and wrapped within a resin 406.

Optionally, fibers 402 may be other fiberglass fibers.

In yet a further embodiment shown in FIGS. 14 and 14A, fibers 502 are generally axially aligned.

As shown in FIG. 13C in the preferable version, the fibers 402 are silica base fibers having a pure silica core 404 of $SiO_2$. An example of the silica based fibers is from Polymicro Technologies Inc. of Phoenix, Ariz.

The coating 405 is a coating of a plastic polymer. The coating 405 can optionally be made to leak light therethrough by etching or scoring, so that it can pull light out transversally through the edge of the root. This is beneficial when using a light sensitive adhesive which reacts to light. The light activating dental cement in the root adjacent to the posts may be a bonding light cement, such as light activating dental cements include chemical resin such as SCOTCH BOND® of 3M Corporation of Saint Paul, Minn.

In this embodiment, the silica core 404 is coated with coating 405, such as KYNAR® brand PVDF (polyvinylidene fluoride), which meets USP class VI pharmaceutical standards. KYNAR® (polyvinylidene fluoride) is a fluoro-polymer which is strong, as reflected by its tensile properties and impact strength, and it has excellent resistance to fatigue. According to ASTM test D638, it has tensile strength of 5,000 to 6,500 psi yield. They have a tensile modulus according to ASTM test D882 of 150 to $200 \times 10^3$ psi. Moreover the crystalline state of the KYNAR® (polyvinylidene fluoride) resins can be modified in rapid cooling to promote smaller crystalline size with increased crystallinity of their higher values for yield strengths than modulus and hardness.

Other resins, such as vinyl esters, acrylates or other polymer plastics may work as well as KYNAR® (polyvinylidene fluoride) brand resin, with different FDA ratings.

Based on the following calculations, while the diameter of each fiber 402 may vary, for a post having a diameter of about 0.040 inches, each fiber 402 is preferably about 60 microns in diameter. In that case, post 401 has about 215 fibers 402 in a post 401 having a diameter of 0.04. For a post 401 having a diameter of 0.050 inches, each fiber 402 is also preferably 60 microns in diameter. Therefore, post 401, with a diameter of 0.05 inches, has about 336 fibers 402.

However, the diameter of fibers 402 can be reduced or enlarged, thus increasing or decreasing the number of fibers 402 within a cross sectional area of post 401.

As noted, the diameter of post 401 will be about 0.05 inch, being made up with a plurality of fibers 402 plus the saturation of an epoxy binder 406 surrounding fibers 402. Epoxy resin 406 may have an optional colorant/opaquer mixed into the epoxy resin.

A preferred embodiment for an epoxy resin is the MASTER BOND® Polymer System EP21LV of Master Bond, Inc. of Hackensack, N.J. MASTER BOND® is a two component, low viscosity epoxy resin in which the fibers are cast. The rigidity of MASTER BOND® can be adjusted by adjusting the mix ratio of the two components.

The number of fibers 402 can be reduced, as long as the amount of epoxy resin binder 406 is altered, to increase or decrease the flexibility of the post 401, with a concomitant increase or decrease of the number of fibers.

For optical fibers 402 of about 60 microns, the radius is about 30 microns and the area of each optical fiber is $900 \times 3.14 = 28.27$ sq. microns. If one uses "n" to equal the number of optical fibers 402, then $n \times 28.27$ is the total area of all the 60 micron filaments in the group (when one is looking at a cross section of post 401). These dimensions are applicable even if posts 401 are twisted or braided, etc.

The total area of a 0.05 inch diameter post in cross section in sq. microns becomes:

0.05×25.4=1.27 millimeters–1270 microns diameter, which includes a 635 micron radius. Therefore where radius=R^3.14×635×635=1.27×10⁶ sq. microns. Therefore, the amount of epoxy and opaquer needed to surround all the optical fibers 402 in post 401=pi(R^×R^)–pi (R*×R*)n. The "pi" can be factored out.

Accordingly, as the R* increases in value and the R^ remains constant, there will be less epoxy/opaquer mixture in the interfilament spaces.

One way to increase the epoxy/opaquer mixture would be to increase the value of R^ in relation to the R*.

Using this relation, one could adjust the mechanical and optical properties of the posts and pins. Accordingly, there are epoxies on the market whose modulus of flexibility can be altered by simply changing the ratio of fibers 402 to epoxy resin 406.

Another factor to be considered is creating an outer skin of epoxy surrounding post 401 of any embodiment, is that epoxy resin 406 be left clear to transmit light. This dimension =pi(R^×R^)–pi(R^–z)x(R^–z), where R^ is the radius of the entire post 402, including the skin coat "z" represents the thickness of the skin coat.

Preferably the post 401 of the bundle of fibers 402 includes a rounded end, and post 401 may optionally be polished at one end to direct light axially therethrough. Post 401 may also have a taper.

As shown in FIGS. 13D and 13E, post 401 may be provided with an optional continuous groove or facet 407 of about 50 to 100 micron in depth to increase surface texturing and to counteract rotation of post 401 within a tooth canal.

The standard length of the post 401 is ⅝ inch and the standard diameter is 0.04 inch to 0.05 inch with an optional taper at the top with ⅛ inch linearly. The texturing may be by sand blasting or by die drawn surface cut, such as at least one groove or facet 407, across linearly or axially of about 50 to 100 micron depth or it may be etched with acid or laser lights such as carbon dioxide laser or Yag laser or there may be an outer skin sheath added which is texturized. Preferably, the individual fibers 402 in one post 401 in bundles are twisted as they come off a spool.

As shown in FIG. 15, another use for which the posts may be used for is as a dental cavity pin 601 to replace titanium, steel, or gold pins which tend to corrode and which do not have a good modulus of elasticity. Optionally the pin 601 may be tooth colored by adding barium sulfate to the epoxy resin that holds the bundle of fibers together, such as in a medical grade epoxy such as bisGMA. The optional pin 601 for teeth with large areas of decay or traumatic damage may be reconstructed, using pins 601 as a lattice scaffolding to stabilize the filling. The flexible pin 601 of the present invention can be looped around and closed into the pin wherein the canal is back filled with composite material. The looping helps with retention by exerting a lateral force against the inside of the canal to provide an anti-rotational feature for the pin 601, if an axially extending surface facet is cut. Other possible uses of pin 601 is for hip prosthesis, or other bone implants or pinned fractures to reduce resorption bone dissolution due to stress or infections. Alternative coatings of pins 601, such as titanium oxide, into the epoxy resin, to facilitate biochemical bonding of the pin 601 to bone.

The flexible posts of the present invention also leads to improved methods of endodontia that eliminate drilling for post placement.

Figure 16A:
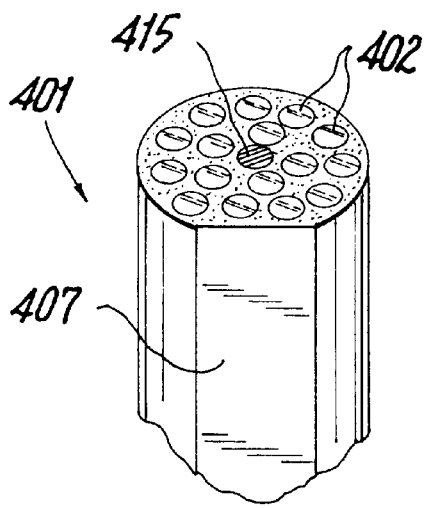
FIG. 16A is a close-up perspective view of the embodiment shown in FIG. 13D with a single central wire.
Figure 16B:
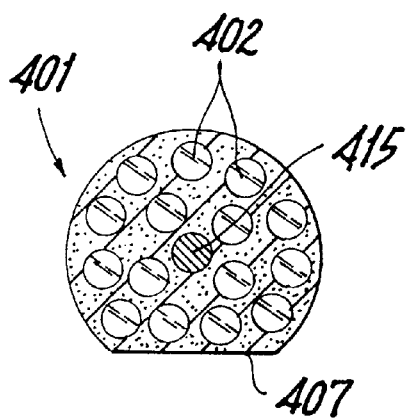
FIG. 16B is a cross sectional plan view of the embodiment shown in FIG. 16A.
Figure 17:
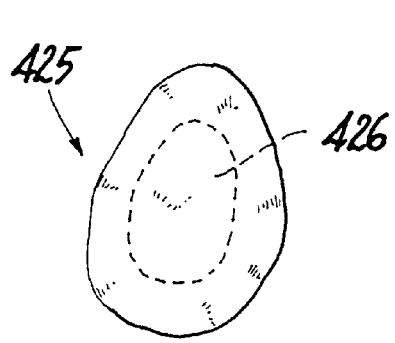
FIG. 17 is a top view of a cuspid tooth showing the outline of an oblong canal.
Figure 17A:
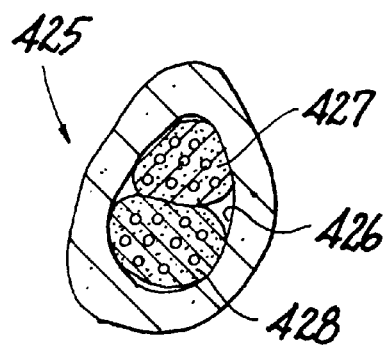
FIG. 17A is a top view of a cuspid tooth with the crown removed and two posts filling the oblong canal.
Figure 17B:
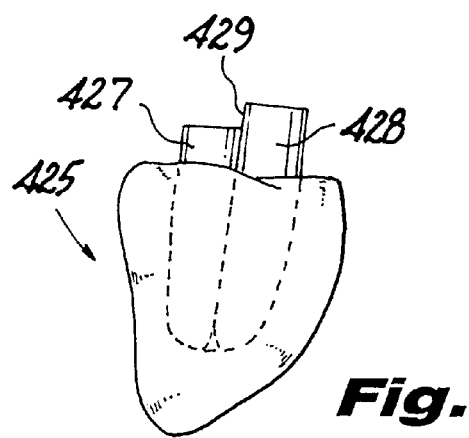
FIG. 17B is a sagital view of a cuspid tooth with the crown removed and two posts in the oblong canal.

FIGS. 16A and 16B show the substitution of a single wire 415 for one of the fibers 402. The use of one or more metal wires renders the post 401 radiopaque. The wire 415 may be alloyed titanium, steel, platinum, palladium or the like. By placing the wire 415 at or near the center, it can be pulled out to facilitate removal of the post. Typically 0.004" in diameter, the wire (once removed) would leave a pilot hole for guidance of a reamer that can be used to remove the post FIG. 17 shows a top view of a cuspid tooth 425 with the outline of an oblong canal 426. Such an oblong shape is difficult to fill adequately with a standard post. Other shapes with irregularities may be difficult to fill as well with a single post. FIG. 17A shows the same tooth 425 with the crown removed and two faceted posts, 427 and 428, almost completely filling area 426 as defined by the oblong canal. FIG. 17B shows a sagital view of this arrangement illustrating the good fit that can be achieved with two posts with facets 429 butted together to lock them in an anti-rotation configuration. By matching two or more faceted standard sized posts, many different sized and shaped tooth canals can be optimally accommodated.

Various changes, additions and modifications of the present invention may be made to the preferred embodiments without departing from the spirit and scope of the present disclosure. Such changes, additions and modifications within a fair reading of the following claims are intended to be part of the present invention.

What is claimed is:

1. An endodontic dental reinforcement post for endodontic and reconstructive pin therapy comprising a prefabricated bundle of non-woven, unstretched and unstressed fibers in a cured resin, said fibers and resin being inelastic and flexible, said post adapted to extend from an apical end to a coronal end of a tooth canal.

2. The dental reinforcement post as in claim 1 wherein said fibers are fiberglass fibers.

3. The dental reinforcement lost as in claim 2 wherein said fiberglass fibers are E-glass fibers.

4. The dental reinforcement as in claim 1 wherein each fiber comprises a plurality of fiber optic filaments.

5. The dental reinforcement post as in claim 1 wherein said bundle of fibers is about 0.05 inch in diameter.

6. The dental reinforcement post as in claim 1 further comprising an epoxy binder.

7. The dental reinforcement post as in claim 6 wherein said epoxy resin further comprises an opaquer composition therein.

8. The dental reinforcement post as in claim 1 wherein said bundle of fibers have a rounded end.

9. The dental reinforcement post as in claim 1 wherein said bundle of fibers have a tapered end.

10. The dental reinforcement lost as in claim 1 further comprising at least one surface cut of about 50 to 100 micron depth to increase texturing.

11. The dental reinforcement post as in claim 10 further comprises at least one axially extending die drawn indentation of 50 to 100 micron, depth to increase texturing.

12. The dental reinforcement post as in claim 10 wherein said texturing is etched with acid.

13. The dental reinforcement post as in claim 10 wherein said texturing is by sandblasting of said reinforcement member.

14. The dental reinforcement post as in claim 10 wherein said texturing is by laser light.

15. The dental reinforcement post as in claim 1 further comprising at least one facet of about 50 to 100 micron depth to increase texturing.

16. The dental reinforcement post as in claim 1 further comprising at least one groove of about 50 to 100 micron depth to increase texturing.

17. The dental reinforcement post as in claim 1 further comprising at least indentation of about 50 to 100 micron depth to increase texturing.

18. The dental reinforcement post as in claim 1 wherein said post is a dental reconstructive pin.

19. The dental reinforcement lost as in claim 18 wherein said dental reconstructive pin is looped.

20. The dental reinforcement post as in claim 1 wherein said post is polished at one end to direct light axially therethrough.

21. The dental reinforcement post as in claim 1 wherein said dental reinforcement post comprises a plurality of adjacent coaxially extending dental reinforcement posts.

22. The dental reinforcement post as in claim 21 wherein each adjacent co-axially extending dental reinforcement post includes at least one axially extending facet abutting a further axially extending facet of a further adjacent coaxially extending dental reinforcement post for locking said plurality of adjacent coaxially extending dental reinforcement posts in position within an interior canal of a tooth.

23. The endodontic dental reinforcement post as in claim 1 wherein said post has a flexibility closely approximating the flexibility of a tooth structure.

24. The endodontic dental reinforcement post as in claim 1 wherein said post is cylindrical.

25. The dental post and core inelastic post as in claim 1 wherein said post is tapered.

26. A dental post and core device comprising an inelastic post, said post having a coronal end and an apical end, said post including a prefabricated plurality of non-woven, unstretched and unstressed fibers in a cured resin, said fibers and resin being inelastic and flexible, said fibers extending between the coronal and the apical end of said post.

27. The dental post and core inelastic post as in claim 26 wherein said post has a flexibility closely approximating the flexibility of a tooth structure.

28. The endodontic dental reinforcement post as in claim 26 wherein said post is cylindrical.

29. The dental post and core inelastic post as in claim 26 wherein said post is tapered.

* * * * *